United States Patent
Chou et al.

(10) Patent No.: US 8,581,979 B2
(45) Date of Patent: Nov. 12, 2013

(54) SYSTEM AND METHOD FOR CONSTRUCTING HIGH RESOLUTION IMAGES

(75) Inventors: Sen Yih Chou, Hsinchu (TW); Chia Hung Cho, Keelung (TW)

(73) Assignee: Industrial Technology Research Institute, Hsinchu (TW)

( * ) Notice: Subject to any disclaimer, the term of this patent is extended or adjusted under 35 U.S.C. 154(b) by 240 days.

(21) Appl. No.: 13/087,626

(22) Filed: Apr. 15, 2011

(65) Prior Publication Data
US 2012/0154574 A1 Jun. 21, 2012

(30) Foreign Application Priority Data

Dec. 16, 2010 (TW) .............................. 99144144 A

(51) Int. Cl.
*G02B 11/22* (2006.01)
*G02B 26/0841* (2006.01)
*B23K 26/067* (2006.01)

(52) U.S. Cl.
USPC ................... 348/135; 359/223.1; 359/224.1; 359/224.2

(58) Field of Classification Search
USPC .............................. 348/135; 359/223.1–224.2
See application file for complete search history.

(56) References Cited

U.S. PATENT DOCUMENTS

| | | | |
|---|---|---|---|
| 5,838,428 A | 11/1998 | Pipitone et al. | |
| 6,753,876 B2 | 6/2004 | Brooksby et al. | |
| 7,274,470 B2 | 9/2007 | Lemelin et al. | |
| 2003/0035123 A1* | 2/2003 | Ramanujan et al. | 358/1.4 |
| 2006/0221783 A1 | 10/2006 | Nagata et al. | |
| 2008/0192231 A1* | 8/2008 | Jureller et al. | 356/36 |
| 2009/0296205 A1* | 12/2009 | Ouchi | 359/370 |

OTHER PUBLICATIONS

Giovanna Sansoni et al., "Development and characterization of a 3D measuring system based on integration of gray code and phase shift light projection," Via Branze 40, 1-25 123 Brescia—Italy, p. 139-147. SPIE vol. 3023.
Javier Vargas, Juan Antonio Quiroga, "Novel multiresolution approach for an adaptive structured light system", Optical Engineering, Feb. 2008, p. 023601-1 to 023601-9, vol. 47(2).
Xu Li, Zeng Dan, Zhang Zhijiang, Wu Yiwen, "Alternate time-space coding for structured light system", Optical Engineering, Dec. 2008, p. 127201-1 to 127201-10, vol. 47(12).
Boxiong Wang, Wei Xiao, Xiuzhi Luo, "New structured light encoding method for range-data acquisition", Optical Engineering, Nov. 2001, p. 2474-2479, vol. 40(11).
Office Action issued on Jul. 31, 2013 for Taiwanese counterpart application.

\* cited by examiner

*Primary Examiner* — David Czekaj
*Assistant Examiner* — Tsion B Owens
(74) *Attorney, Agent, or Firm* — Egbert Law Offices, PLLC

(57) ABSTRACT

A system for constructing high resolution images includes a beam splitter assembly, a light intensity modulator, an image capturing module and an image processing module. The beam splitter assembly is utilized to reflect a light beam generated from a light source generating device and generate a splitting beam. The light intensity modulator is utilized to modulate the intensity of the splitting beam to generate a modulating beam, which includes a predetermined noise. The modulating beam is emitted onto an object to generate a modulating image. The image capturing module is utilized to obtain a plurality of modulating images. The image processing module is utilized to analyze the modulating images to generate a high resolution image.

28 Claims, 9 Drawing Sheets

SYSTEM AND METHOD FOR CONSTRUCTING HIGH RESOLUTION IMAGES

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The disclosure relates to a system and a method for capturing images. Particularly, the disclosure relates to a system and a method for constructing high resolution images.

2. Description of Related Art Including Information Disclosed Under 37 CFR 1.97 and 37 CFR 1.98

In current optical measurement systems, if the surface of the object under test is uneven or composed of inconsistent material, the light intensity of the reflected light beam or scattering light beam on the surface will vary. Thus, it is required to use a single point capturing device with high dynamic range to obtain the accurate intensity of the reflected light beam. However, when we use the single point capturing device to measure a wide range, the device translocation needs to be controlled by a high-precision device. In addition, such devices require longer periods of time to detect larger measurement areas.

Moiré interferometry technology is currently applied for surface measurements of over 10 μm scale. Moiré interferometry technology is used to measure three dimensional appearance of the surface. The resolution of the Moiré interferometry is determined by the fineness of interference fringes. Traditionally, in order to increase the fineness of the interference fringes, scientists use certain special fringe encoding techniques such as DeBruijn space encoding technique and Gray time encoding technique. Although such techniques can provide efficient measurements, Moiré interferometry technology needs to be improved to measure objects under 10 μm scale.

In addition, when the system uses charge-coupled sensors or complementary metal oxide semiconductor sensors to measure large areas and uses high resolution technique such as white light interference technique, the measuring speed of the system may not be as fast as that of systems using Moiré interferometry technology.

U.S. Pat. No. 6,753,876 discloses a method for constructing high dynamic images for overcoming the low measuring speed. The method can adjust the light intensity, capture the image data, set up the standard image under the predetermined light intensity, and analyze whether the intensity of each pixel is over the saturation region or under the noise floor. If one pixel is over the saturation region, the method will replace it with a pixel that has lower light intensity and does not exceed the saturation region. Alternatively, if one pixel is below the noise floor, the method will replace it with a pixel that has a higher light intensity and is over the noise floor. Although the technique disclosed in U.S. Pat. No. 6,753,876 can increase measurement speed, a system and method for constructing high resolution images are still desired.

BRIEF SUMMARY OF THE INVENTION

A system and a method for constructing high resolution images are disclosed. The system includes a beam splitter assembly, a light intensity modulator, an image capturing module, and an image processing module. The beam splitter reflects an input light beam to generate a splitting beam. The light intensity modulator modulates the intensity of the splitting beam to generate a modulating beam, including a predetermined noise. The modulating beam is emitted onto an object to generate a modulating image. The image capturing module obtains a plurality of the modulating images. The image processing module analyzes the modulating images to generate a high resolution image.

A system for constructing high resolution images is disclosed. The system includes a beam splitter assembly, an image capturing module, and an image processing module. The beam splitter assembly conducts a modulating beam including a predetermined noise onto an object to generate a modulating image. The image capturing module obtains a plurality of the modulating images. The image processing module analyzes the modulating images to generate a high resolution image.

A method for constructing high resolution images includes the following steps: providing a light beam, a modulating beam, and a grating, wherein the light beam and the modulating beam pass through the grating to project onto an object, and the modulating beam includes a predetermined noise; emitting the light beam and the modulating beam onto the object to obtain a plurality of modulating images of the object; and analyzing the modulating images to generate a high resolution image.

Other purposes of the disclosure are disclosed in the following description, easily anticipated in the present specification, and taught in detailed description in the present application. All described paragraphs in the disclosure can be realized in view of the components and assembly thereof indicated in the claims. It should be noted that the above-mentioned description and the detailed description that follows only indicate, but are not limited to, the embodiment of the disclosure.

The foregoing has outlined rather broadly the features and technical benefits of the disclosure in order that the detailed description of the invention that follows may be better understood. Additional features and benefits of the invention will be described hereinafter, and form the subject of the claims of the invention. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the invention as set forth in the appended claims.

BRIEF DESCRIPTION OF THE SEVERAL VIEWS OF THE DRAWINGS

The accompanying drawings, which are incorporated in and constitute a part of this specification, illustrate embodiments of the disclosure and, together with the description, serve to explain the principles of the invention.

DETAILED DESCRIPTION OF THE INVENTION

The following description of the disclosure accompanies drawings, which are incorporated in and constitute a part of this specification, and illustrate embodiments of the disclosure, but are not limited to the embodiments. In addition, the following embodiments can be properly integrated to complete another embodiment.

Figure 1:
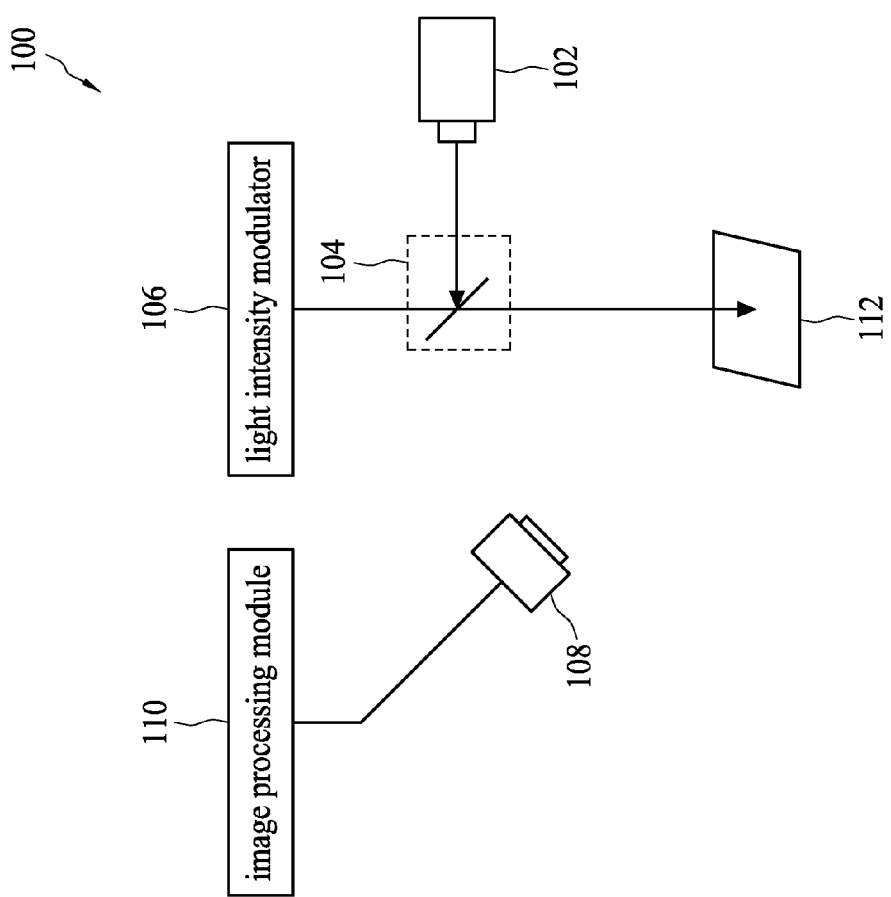
FIG. 1 shows a perspective view illustrating a system for constructing high resolution images according to one exemplary embodiment of the disclosure.

According to one exemplary embodiment shown in FIG. 1, the system 100 for constructing high resolution images comprises a light source generating device 102, a beam splitter assembly 104, a light intensity modulator 106, an image capturing module 108, and an image processing module 110. The light source generating device 102 generates a light beam. Based on the disclosure, the light beam is a collimating beam. The beam splitter assembly 104 reflects the light beam to generate a splitting beam emitting into the light intensity modulator 106 so that the light intensity modulator 106 modulates the intensity of the splitting beam to generate a modulating beam. Particularly, the beam splitter assembly 104 reflects the light beam into the light intensity modulator 106. Since the light intensity modulator 106 is capable of mixing the predetermined noise and the splitting beam to generate the modulating beam by modulating the intensity of the splitting beam, the difference between the modulating beam and the splitting beam is that the modulating beam includes predetermined noise, which does not exist in the splitting beam. In this embodiment, the modulating beam passes through the beam splitter assembly 104 to project onto an object 112 to generate a modulating image. Thus, the modulating image is generated by projecting only the modulating beam onto the object 112. However, the modulating images are not limited to the above-mentioned embodiment. The modulating images can be generated by projecting the modulating beam and the light beam onto the object 112. In the embodiment, the image capturing module 108 obtains a plurality of modulating images. According to the embodiment, the image capturing module 108 can be a charge coupled sensor or a complementary metal oxide semiconductor sensor to obtain the modulating images of the object 112.

The image processing module 110 analyzes the modulating images of the object 112 to generate a high resolution image.

Figure 2:
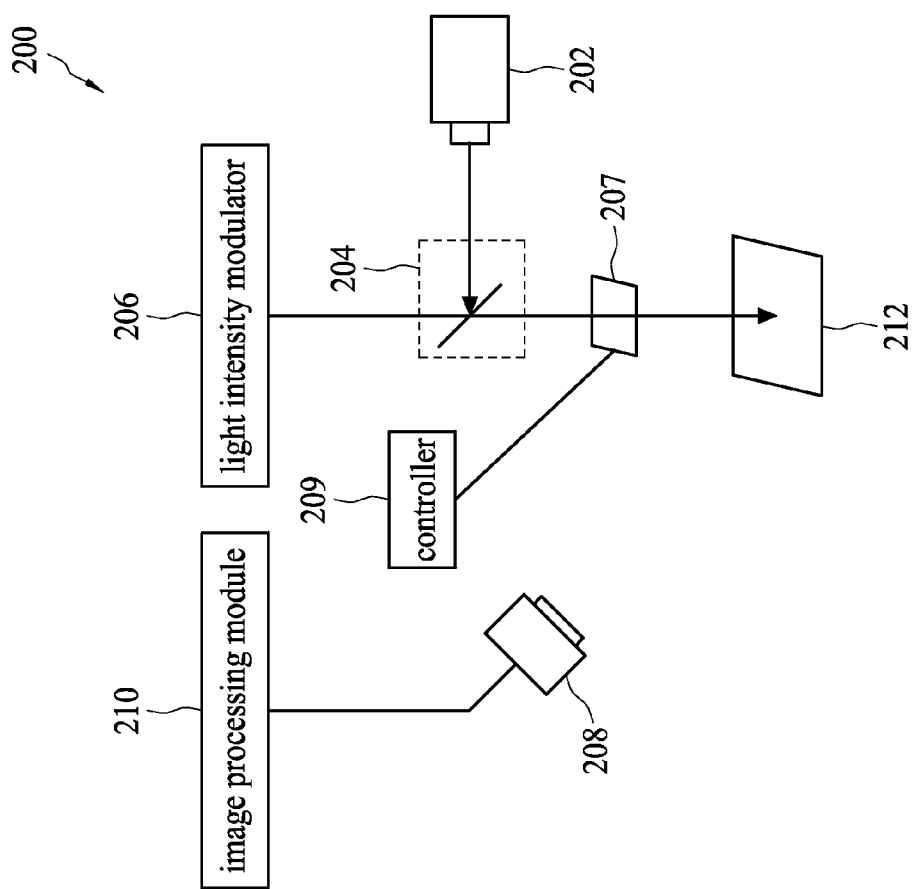
FIG. 2 shows a perspective view illustrating a system for constructing high resolution images according to another exemplary embodiment of the disclosure.

In another embodiment shown in FIG. 2, a system 200 for constructing high resolution images comprises a light source generating device 202, a beam splitter assembly 204, a light intensity modulator 206, a grating 207, an image capturing module 208, a controller 209, and an image processing module 210. The light source generating device 202 generates a light beam. One part of the light beam passes through the beam splitter assembly 204, while the other part of the light beam is reflected by the beam splitter assembly 204 to generate a splitting beam, which is emitted into the light intensity modulator 206. In the system 200, the light intensity modulator 206 is selected from the group consisting of a reflected light intensity modulator and a transmitted light intensity modulator. The reflected light intensity modulator is further selected from the group consisting of a liquid crystal on silicon (LCos) device, a digital micromirror device (DMD), and a digital light processing device (DLP). The transmitted light intensity modulator includes a liquid crystal unit. In this embodiment, the light intensity modulator 206 preferably is the liquid crystal on silicon device of the reflected light intensity modulator; however, in another embodiment, the light intensity modulator 206 can utilize the transmitted light intensity modulator or other modified modulators according to different design requirements.

Referring to the embodiment shown in FIG. 2, the splitting beam is modulated by the light intensity modulator 206, which modulates the intensity of the splitting beam by mixing the predetermined noise and the splitting beam to generate a modulating beam. Since the reflected light intensity modulator not only modulates the splitting beam but can also reflect the splitting beam, the splitting beam is transformed to the modulating beam, which is emitted to the beam splitter assembly 204. The beam splitter assembly 204 allows the partial modulating beam to pass through the grating 207, which diffracts the modulating beam to generate an interference fringe projecting onto the object 212.

Figure 3:
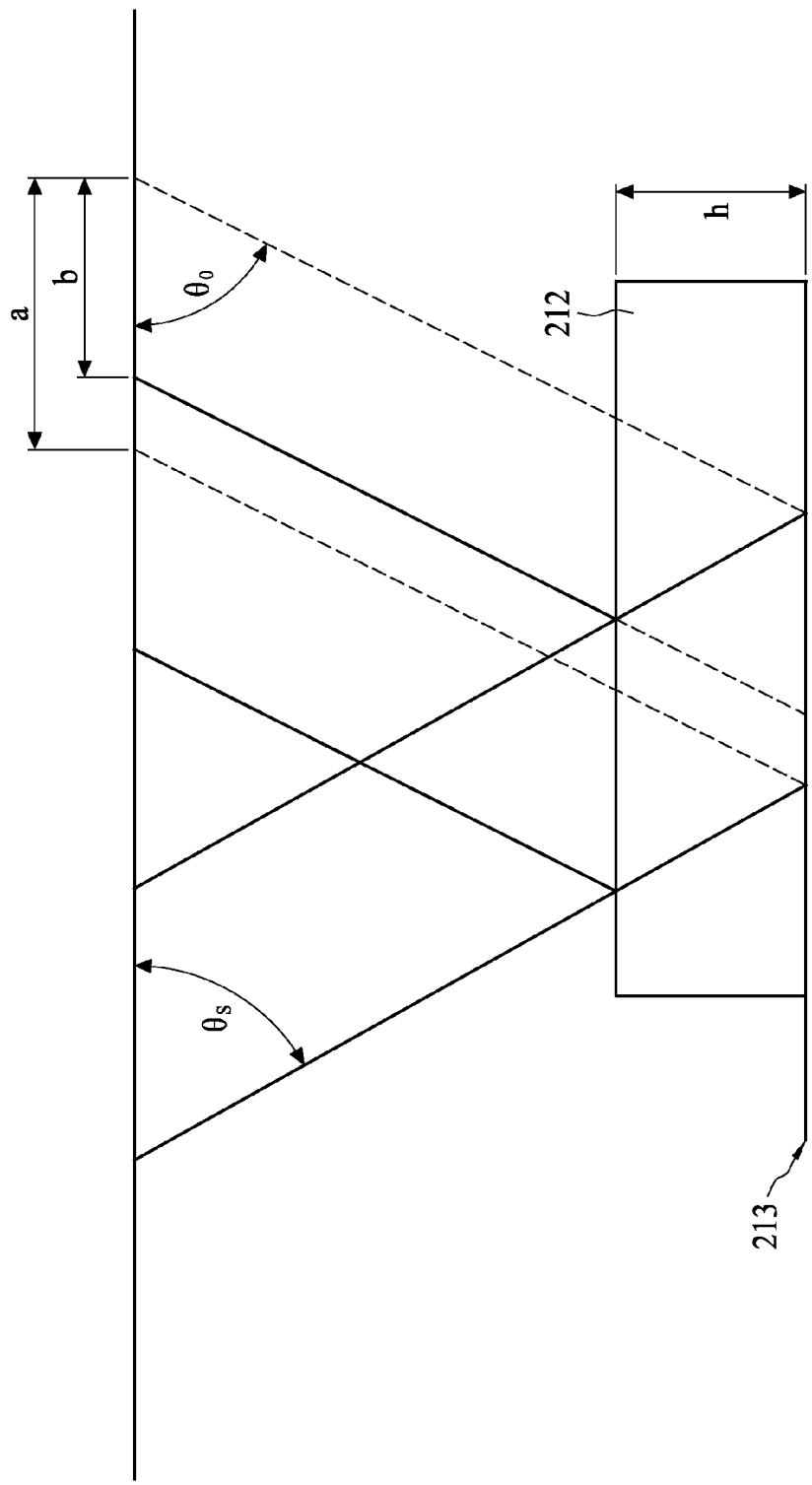
FIG. 3 shows a perspective view illustrating the modulating beam projection on the object.

Referring to FIG. 3, the modulating beam passes through the grating (not shown) to be emitted onto the object 212 with an inclination angle $\theta_s$ and then to be received by an image capturing module 208 (such as a charge coupled device) with another inclination angle $\theta_0$ based on the reference surface 213. From the viewpoint of the image capturing module 208, the interference fringe of the modulating beam has an original width a. After the object 212 is presented, the width a of the interference fringe has changed to a width b. Based on the formula (1), the height of the object 212 can be estimated.

$$h = \frac{\tan\theta_s \tan\theta_o}{\tan\theta_0 + \tan\theta_s} \times b \qquad (1)$$

Particularly, the controller 209 generates a grating translocation signal to control the translocation of the grating 207. After the grating 207 is translocated, the image capturing module 208 (such as a charge coupled device) receives the modulating images prior to the grating 207 translocation or after the grating 207 translocation and transmits the modulating images to the image processing module 210 for constructing the phase difference b of the object 212 so as to estimate the height h of the object 212.

Figure 4:
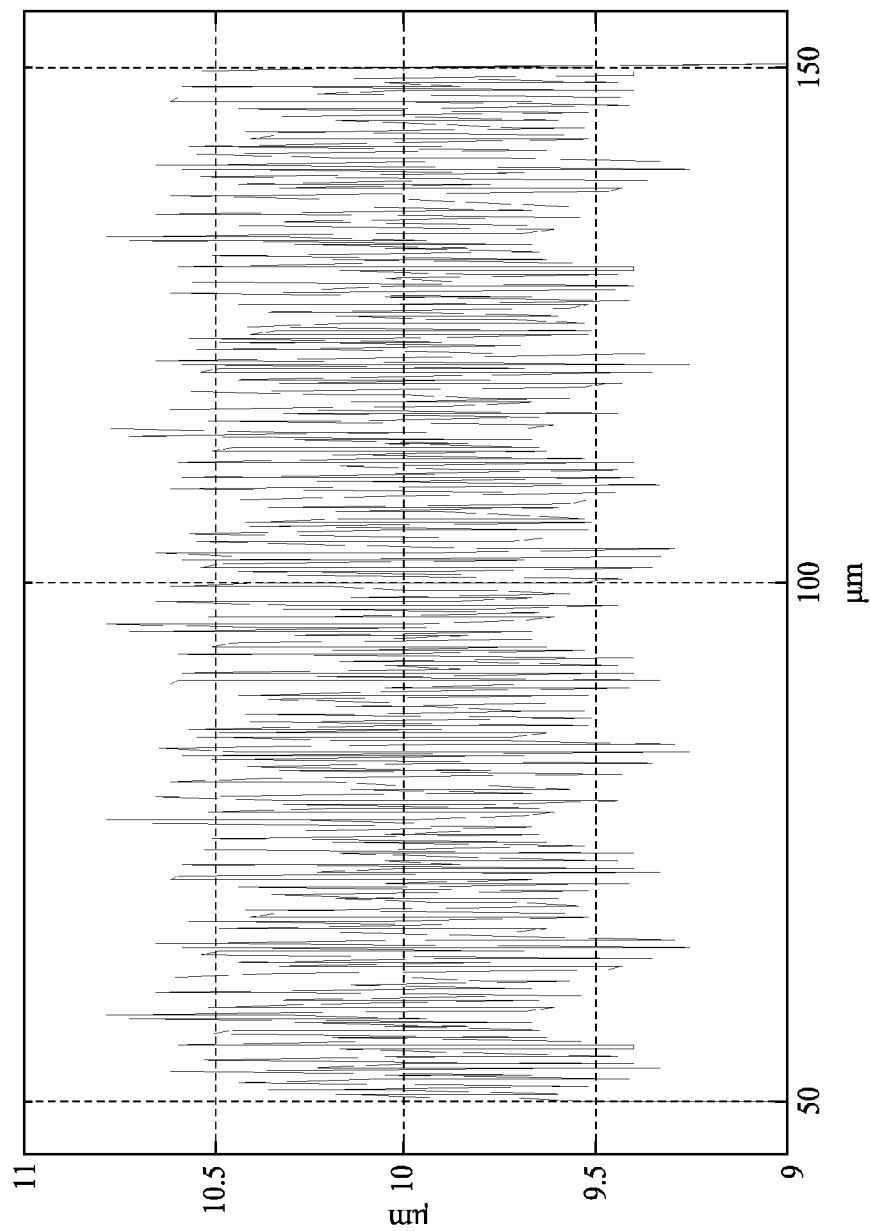
FIG. 4 shows a perspective view illustrating an interference spectrum of the object projected by the light beam.
Figure 5:
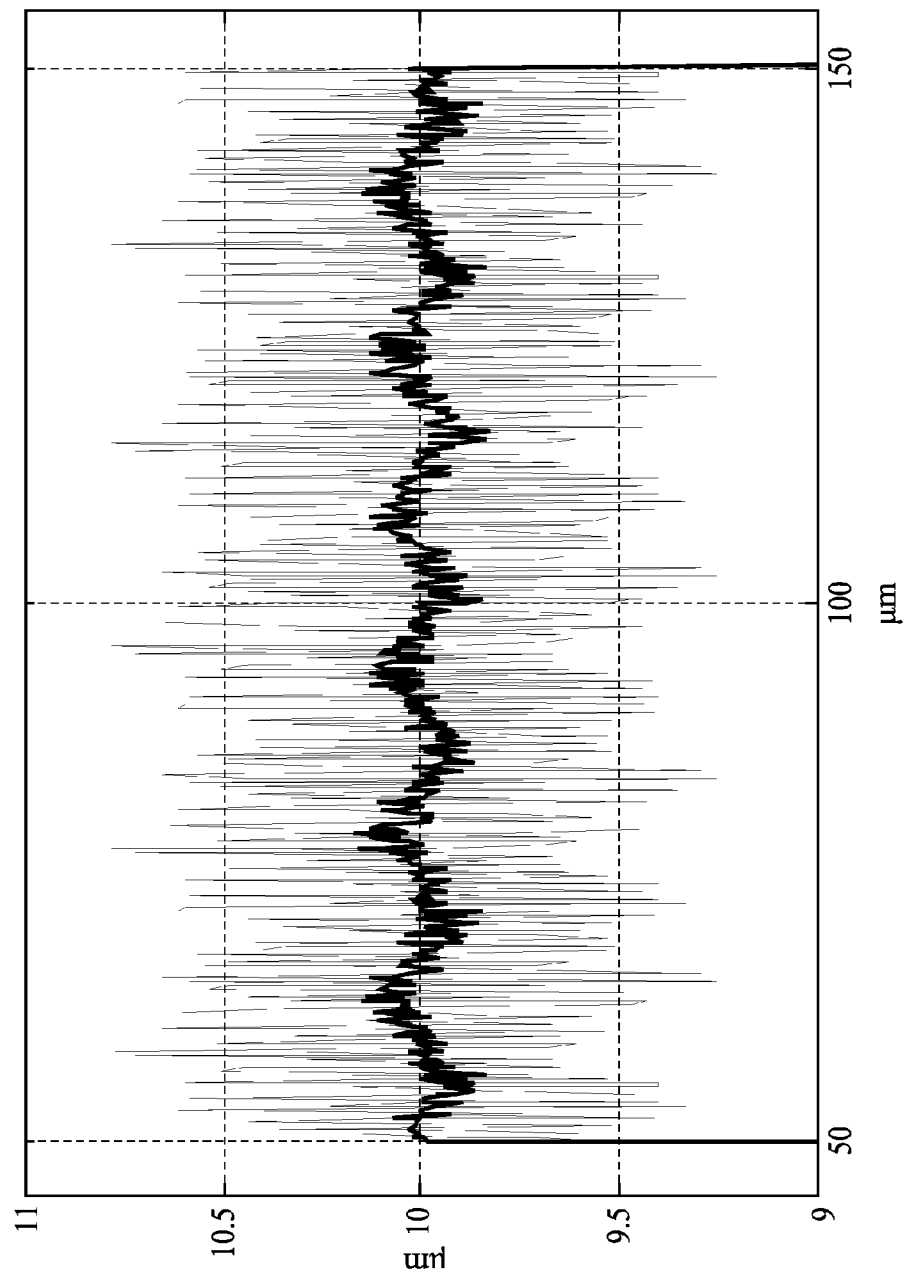
FIG. 5 shows a perspective view illustrating an interference spectrum of the object projected by the modulating beam.

If the optical system is a theoretical system that includes the quantization error of the image capturing module 208 (such as a charge coupled device) and the object 212 has a height h of 10 μm, the theoretical result of the light beam without modulation passing through the grating 207 to project the interference fringe on the object 212 can be present in FIG. 4. Obviously, the quantization error of the image capturing module 208 (such as a charge coupled device) causes the deviation of the height h of the object 212 of about ±0.7 μm. The main reason for the above-mentioned deviation is that the resolution of the phase difference b is too low to reduce deviation of the height. In order to increase the resolution of the phase difference b, the light intensity modulator 206 can mix the predetermined noise and the splitting beam to generate the modulating beam. In this embodiment, the predetermined noise is preferably a white noise with a flat power spectral density. After the modulating beam including white noise passes through the grating 207 to project onto the object 212, the image capturing module 208 obtains a plurality of modulating images from the object 212 projected by the modulating beam. The modulating image can be further analyzed by the image processing module 210 to generate a high resolution image. After the controller 209 controls the grating 207 to be translocated, the image capturing module 208 of the system 200 can obtain another high resolution image. The above-mentioned two high resolution images can increase the resolution of the phase difference b, but the number of the high resolution images is not limited to the above-mentioned embodiment. In other words, the system 200 can use at least two high resolution images to increase the resolution of the phase difference b. After the resolution of the phase difference b increases, the deviation of the height h of the object 212 can be efficiently limited to ±0.1 μm as shown in FIG. 5.

Figure 6A:
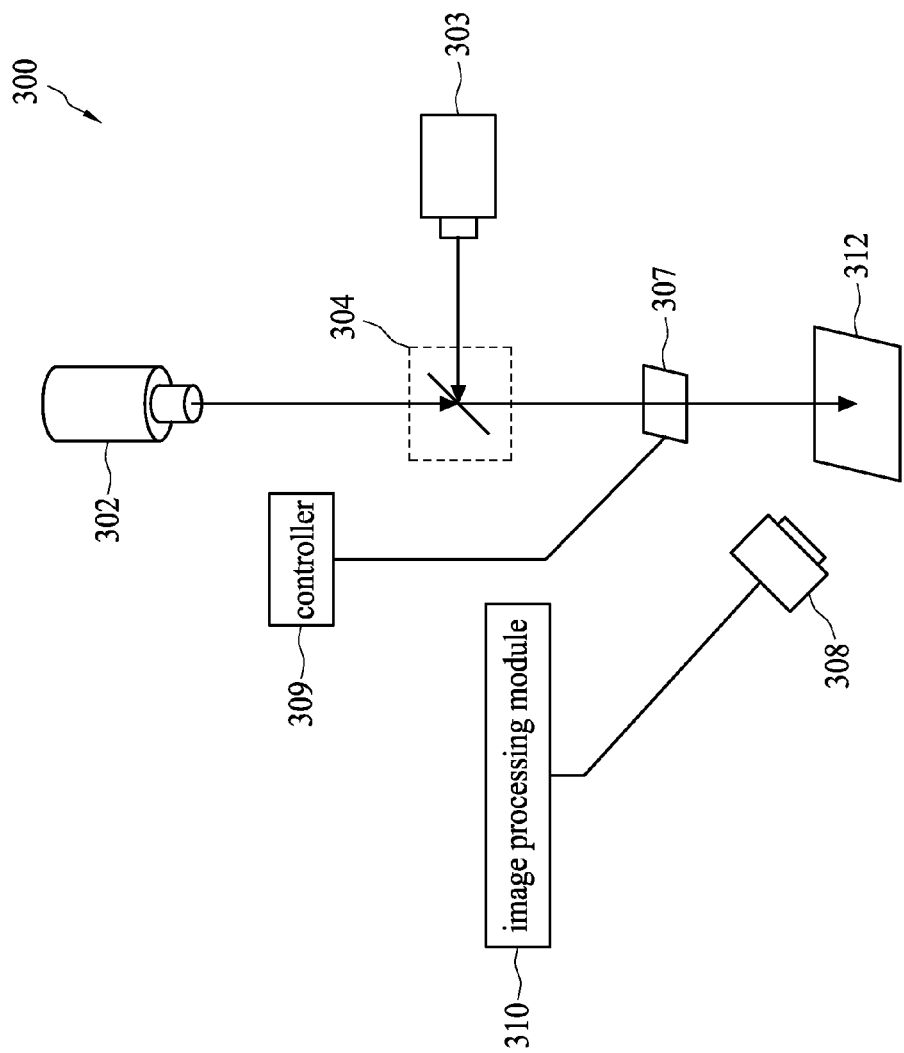
FIG. 6A shows a perspective view illustrating a system for constructing high resolution images according to another exemplary embodiment of the disclosure.

Referring to one embodiment shown in FIG. 6A, a system 300 for constructing high resolution images comprises a first light source generating device 302, a second light source generating device 303, a beam splitter assembly 304, an image capturing module 308, and an image processing module 310. The functions of the beam splitter assembly 304, the image capturing module 308, and the image processing module 310 are similar to the functions of the beam splitter assembly 104, the image capturing module 108, and the image processing module 110. The first light source generating device 302 generates the modulating beam including a predetermined noise. The predetermined noise is preferably a white noise. In this embodiment, the white noise has, but is not limited to, a zero-averaged deviation signal. Since the deviation signal of the white noise averages zero, the result of the multiple sampling of the digital signals including the white noise does not shift. In addition, because the white noise is mixed before the modulating image signal digitalization, the average of the multiple sampling after digitalization will be close to the true value so as to reduce the quantization error during digitalization. In FIG. 5, the system 300 can efficiently limit the quantization error to ±0.1 μm. The second light source generating device 303 generates a light beam with a stable light intensity. In this embodiment, the light beam of the second light source generating device 303 can enhance the intensity of the modulating beam from the first light source generating device 302. However, if the light intensity of the modulating beam is strong enough, the system in another embodiment (not shown) can function without the second light source generating device 303. In the embodiment, the modulating images are generated by projecting the light beam and the modulating beam onto the object 312. However, the modulating image can emit only the modulating beam onto the object 312 to generate the modulating image.

As shown in FIG. 6A, the system 300 further includes a grating 307 and a controller 309 to control the translocation of the grating 307 by generating a grating translocation signal. The grating 307 conducts the light beam to generate interference fringe projecting onto an object 312. After the grating 307 is translocated by the controller 309, the image processing module 310 constructs respective high resolution images prior to the grating 307 translocation or after the grating 307 translocation according to the modulating images prior to the grating 307 translocation or after the grating 307 translocation so as to construct the phase difference b of the object 312 and to precisely estimate the height h of the object 312.

Figure 6B:
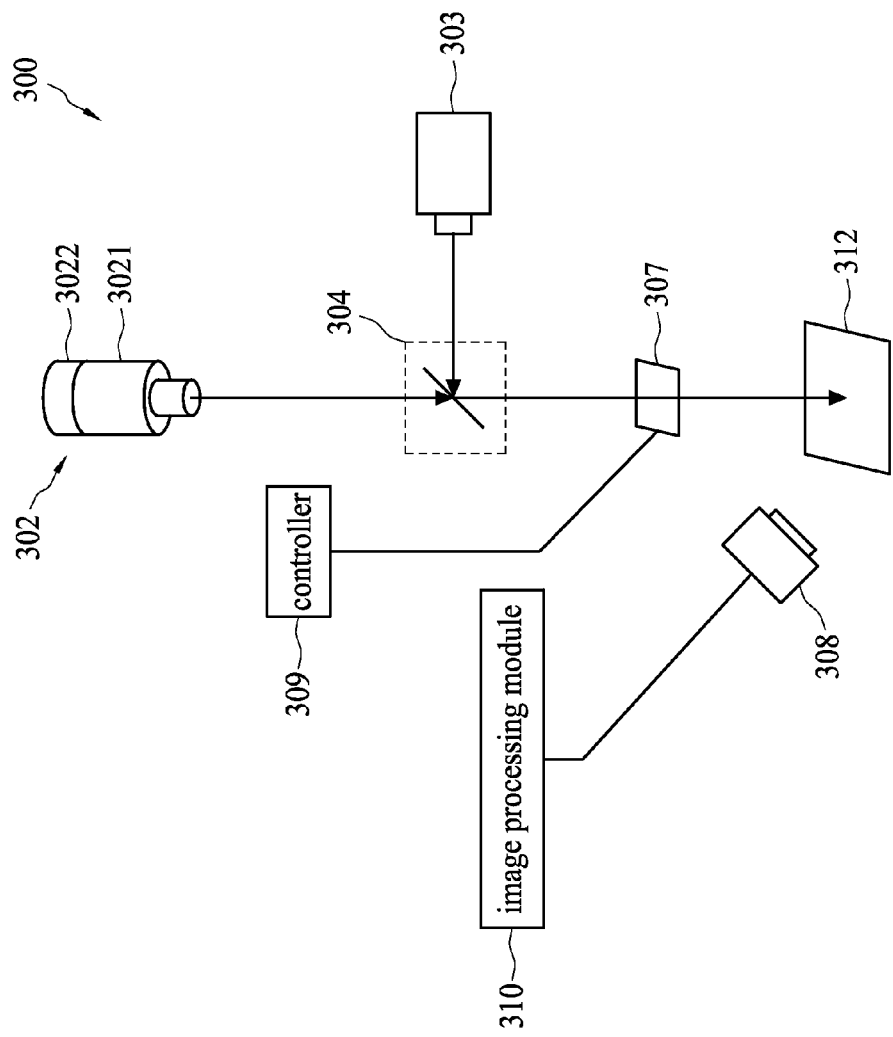
FIG. 6B shows a perspective view illustrating a system for constructing high resolution images according to another exemplary embodiment of the disclosure.

In the embodiment shown in FIG. 6A, the first light source generating device 302 preferably is a dithering light source generating device generating the above-mentioned modulating beam. However, in another embodiment shown in FIG. 6B, the first light source generating device 302 further includes a light source 3021 and a light intensity modulator 3022, which is selected from the group consisting of a reflected light intensity modulator and a transmitted light intensity modulator. The reflected light intensity modulator is further selected from the group consisting of an LCos device, a DMD, and a DLP device. Thus, the first light source generating device 302 can generate the above-mentioned modulating beam by the light beam generated from the light source 3021 and the light beam modulation of the light intensity modulator 3022. In accordance with the embodiment, the image capturing module 308 can be a charge coupled sensor or a complementary metal oxide semiconductor sensor to obtain the modulating images of the object 312.

Figure 7:
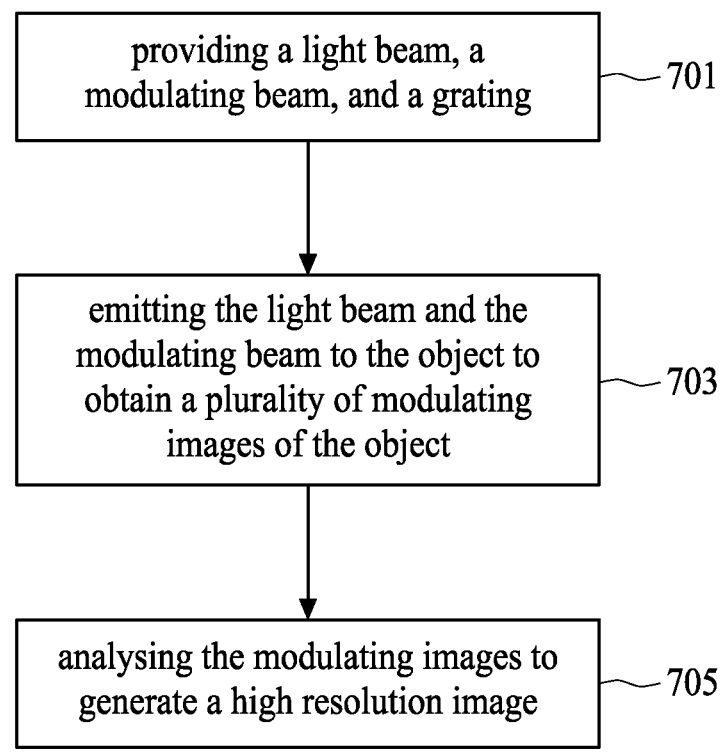
FIG. 7 shows a flow diagram illustrating a method for constructing high resolution images according to one exemplary embodiment of the disclosure.

Based on one exemplary embodiment, FIG. 7 shows a flow diagram illustrating a method for constructing high resolution images. The exemplary embodiment refers to FIG. 2, FIG. 6A, and FIG. 7. Step 701 provides a light beam, a modulating beam, and a grating 307, wherein the light beam and the modulating beam pass through the grating 307 to project onto the object 312, and the modulating beam includes a predetermined noise. The predetermined noise preferably is a white noise with a flat power spectral density or zero-averaged deviation signals. The modulating beam is generated by the first light source generating device 302 (such as a dithering light source generating device), while the light beam is generated by the second light source generating device 303. The light beam and the modulating beam pass through the beam splitter assembly 304 to project onto the object 312. In the embodiment of FIG. 2, the light beam is reflected by the beam splitter assembly 204 toward the light intensity modulator 206 to generate the modulating beam. The light intensity modulator 206 is selected from the group consisting of a reflected light intensity modulator and a transmitted light intensity modulator. The reflected light intensity modulator is further selected from the group consisting of an LCos device and a DMD. If the light intensity modulator 206 is the transmitted light intensity modulator, the light intensity modulator 206 includes a liquid crystal unit.

Step 703 emits the light beam and the modulating beam onto the object 312 to obtain a plurality of modulating images of the object 312 captured by the image capturing module 308. The image capturing module 308 obtaining the modulating images of the object 312 is selected from the group consisting of a charge coupled sensor and a complementary metal oxide semiconductor sensor. Step 705 analyzes the modulating images to generate a high resolution image, wherein step 705 utilizes the image processing module 310 to analyze the modulating images.

The modulating beam receives added white noise with zero-averaged deviation signals before the modulating beam digitalization. After the image capturing module 308 samples the modulating image having white noise with zero-averaged deviation signals, the average of the modulating image signal will increase the number of digits to reduce the magnitude of possible round-off errors to approximate the true value. Since white noise is added before the modulating image digitalization, the average of the modulating image signal after digitalization will reduce the magnitude of possible quantization errors due to the modulating image digitalization. Therefore, the image processing module 310 generates a high resolution image after the modulating image digitalization.

Figure 8:
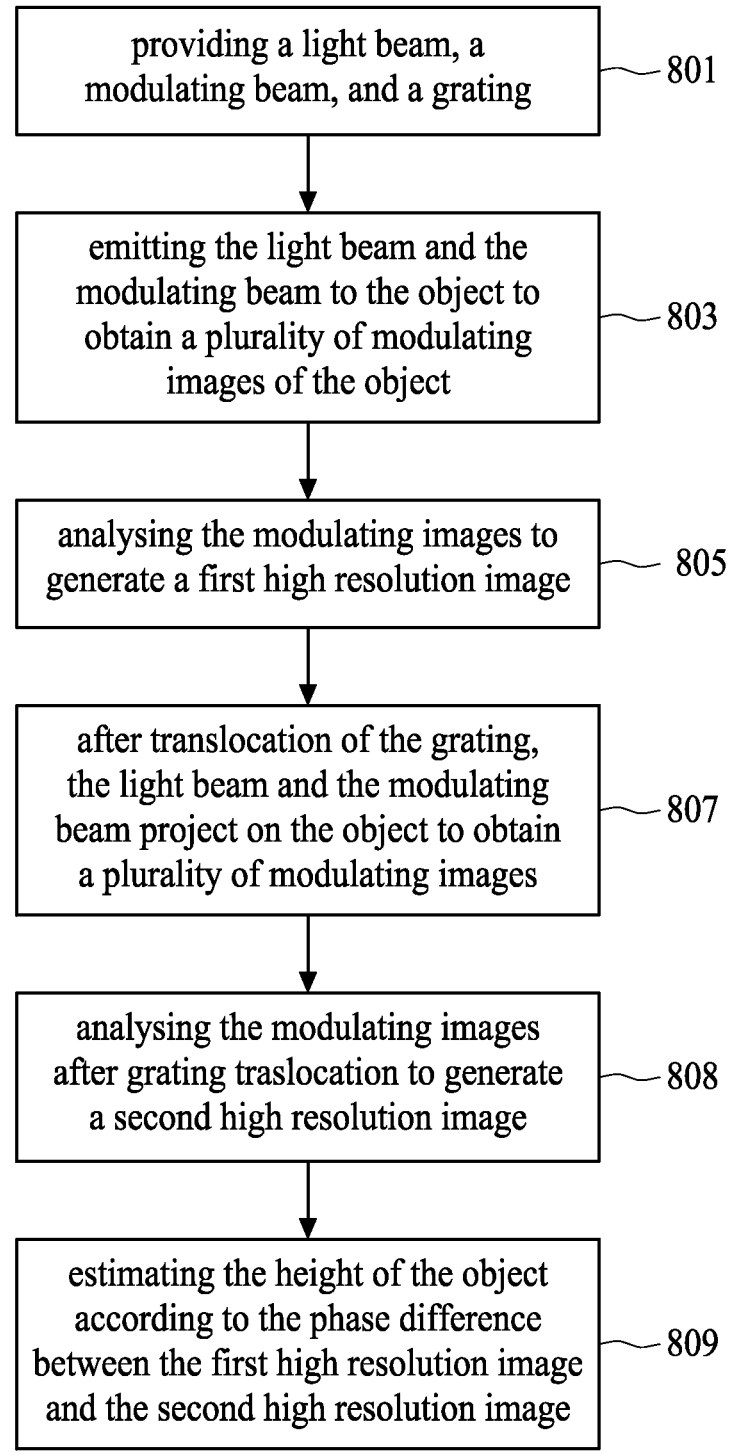
FIG. 8 shows a flow diagram illustrating a method for estimating a height of an object by high resolution images according to one exemplary embodiment of the disclosure.

FIG. 8 shows a flow diagram illustrating a method for estimating a height of an object by high resolution images according to one exemplary embodiment of the disclosure. The exemplary embodiment refers to FIG. 2, FIG. 6A, and FIG. 8. Step 801 and step 803 are similar to step 701 and step 703 shown in the above-mentioned FIG. 7. Both step 805 and step 705 are used to generate high resolution images, but step 805 mainly generates a first high resolution image. In step 807, after the controller 209, 309 translocates the grating 207, 307, the light beam and the modulating beam project onto the object 212, 312 to obtain a plurality of modulating images of the object 212, 312, wherein the modulating image is obtained by the image capturing module 208, 308 in step 803. Next, step 808 utilizes the image processing module 310, 210 to analyze the modulating images after translocation of the grating 207, 307 to obtain a second high resolution image. Finally, in step 809, the image processing module 310, 210 precisely estimates the height h according to the phase difference b between the first high resolution image and the second high resolution image. Through high resolution images, the system 200, 300 can precisely estimate the height h of the object 212, 312 and does not need to spend a lot of time in measurement.

Although the disclosure and its benefits have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the disclosure is not intended to be limited to the particular embodiments of the apparatus, system, machine, device, composition of matter, means, structure and steps described in the specification. As one of ordinary skill in the art will readily appreciate from the disclosure, apparatuses, system, machines, devices, compositions of matter, means, structures, or steps, presently existing or later to be developed, that perform substantially the same function or achieve substantially the same result as the corresponding embodiments described herein may be utilized according to the disclosure. Accordingly, the appended claims are intended to include within their scope such apparatuses, system, machines, device, compositions of matter, means, structures, or steps.

We claim:

1. A system for constructing high resolution images, the system comprising:
    a beam splitter assembly; reflecting an input light beam to generate a splitting beam;
    a light intensity modulator; modulating an intensity of the splitting beam to generate a modulating beam; including a predetermined noise, wherein the modulating beam is emitted onto an object to generate a modulating image;
    a grating, wherein the modulating beam passes through the grating to generate an interference fringe projecting onto the object;
    an image capturing module; obtaining a plurality of modulating images;
    a controller; generating a grating-translocation signal to control the translocation of the grating; and
    an image processing module; analyzing the modulating images to generate a high resolution image, wherein the image processing module constructs a phase difference of the object according to the modulating images prior to the translocation of the grating or after the translocation of the grating.

2. The system of claim 1, wherein the input light beam is generated from a light source generating device.

3. The system of claim 1, wherein the light intensity modulator is selected from the group consisting of a reflected light intensity modulator and a transmitted light intensity modulator.

4. The system of claim 3, wherein the reflected light intensity modulator is selected from the group consisting of a liquid crystal on silicone, a digital micromirror device, and a digital light processing device.

5. The system of claim 3, wherein the transmitted light intensity modulator includes a liquid crystal unit.

6. The system of claim 1, wherein the image capturing module is selected from a group consisting of a charge coupled sensor and a complementary metal oxide semiconductor sensor.

7. The system of claim 1, wherein the predetermined noise is a white noise with a flat power spectral density.

8. A system for constructing high resolution images; the system comprising:
    a beam splitter assembly, conducting a modulating beam including a predetermined noise onto an object to generate a modulating image;
    a grating wherein the modulating beam passes through the grating to generate an interference fringe projecting onto the object;
    an image capturing module; obtaining a plurality of the modulating images;
    a controller generating a grating-translocation signal to control a translocation of the grating; and
    an image processing module; analyzing the modulating image to generate a high resolution image, wherein the image processing module constructs a phase difference of the object according to the modulating images prior to the translocation of the grating or after the trans location of the grating.

9. The system of claim 8, wherein the modulating beam is generated from a first light source generating device.

10. The system of claim 9, further comprising a second light source generating device generating a light beam, wherein the beam splitter assembly reflects the light beam onto the object.

11. The system of claim 10, wherein the beam splitter assembly reflects part of the light beam onto the object and allows part of the modulating beam to pass through the beam splitter assembly to project onto the object.

12. The system of claim 9, wherein the first light source generating device includes a dithering light source generating device; for generating the modulating beam.

13. The system of claim 9, wherein the first light source generating, device includes a light source and a light intensity modulator, said light intensity modulator selected from the group consisting of a reflected light intensity modulator and a transmitted light intensity modulator, the light source generates a light beam, and the light intensity modulator modulates the light beam to generate the modulating beam.

14. The system of claim 13, wherein the reflected light intensity modulator is selected from the group consisting of a liquid, crystal on silicone, a digital nticromirror device, and a digital light processing device.

15. The system of claim 13, wherein the transmitted light intensity modulator includes a liquid crystal unit.

16. The system of claim 10, wherein the image capturing module is selected from a group consisting of a charge coupled sensor and a complementary metal oxide semiconductor sensor.

17. The system of claim 10, wherein the predetermined noise is a white noise.

18. A method for constructing high resolution images, the method comprising the steps of:
providing a light beam; and a modulating beam; and a grating, wherein the light beam and the modulating beam pass through the grating to project onto an object, and the modulating beam includes a predetermined noise;
generating a grating-translocation signal to control a translocation of the grating;
emitting the light beam and the modulating beam onto the object to obtain a plurality of modulating images of the object;
constructing a phase difference of the object according to the modulating images prior to the translocation of the grating or after the translocation of the grating; and
analyzing the modulating images to generate a high resolution image.

19. The method of claim 18, wherein the beam and the modulating beam pass through a beam splitter assembly to project onto the object.

20. The method of claim 18, wherein the modulating beam is generated by a dithering light source generating device.

21. The method of claim 19, wherein the light beam is generated by a light source generating device.

22. The method of claim 21, wherein the light beam passes through the beam splitter assembly to a light intensity modulator; for generating the modulating beam.

23. The method of claim 22, wherein the light intensity modulator is selected from the group consisting of a reflected light intensity modulator and a transmitted light intensity modulator.

24. The method of claim 23, wherein the reflected light intensity modulator includes a liquid crystal on silicone or a digital micromirror device.

25. The method of claim 23, wherein the transmitted light intensity modulator includes an liquid crystal unit.

26. The method of claim 18, wherein the modulating image is captured by an image capturing module.

27. The method of claim 26, wherein the image capturing module is selected from a group consisting of a charge coupled sensor and a complementary metal oxide semiconductor sensor.

28. The method of claim 18, wherein the predetermined noise is a white noise.

* * * * *